US009266847B2

(12) United States Patent
Pham et al.

(10) Patent No.: US 9,266,847 B2
(45) Date of Patent: Feb. 23, 2016

(54) COMPOUNDS, PROBES, AND METHODS OF SYNTHESIS AND METHODS OF IMAGING COX-2-ASSOCIATED DISEASES

(71) Applicant: Vanderbilt University, Nashville, TN (US)

(72) Inventors: Wellington Pham, Brentwood, TN (US); Donald D. Nolting, Nashville, TN (US); John C. Gore, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/074,099

(22) Filed: Nov. 7, 2013

(65) Prior Publication Data

US 2014/0134107 A1    May 15, 2014

Related U.S. Application Data

(60) Provisional application No. 61/724,495, filed on Nov. 9, 2012.

(51) Int. Cl.
*A61K 51/04*     (2006.01)
*C07D 277/28*   (2006.01)

(52) U.S. Cl.
CPC .......... *C07D 277/28* (2013.01); *A61K 51/0453* (2013.01)

(58) Field of Classification Search
CPC ..... A61K 51/04; A61K 31/425; C07D 277/28
USPC ...................... 424/1.37, 1.65, 1.89
See application file for complete search history.

(56) References Cited

U.S. PATENT DOCUMENTS 7,935,852 B2 *   5/2011   Wadsworth et al. .......... 568/651

FOREIGN PATENT DOCUMENTS

JP        11-302266       11/2011
JP        11302266    *  11/2011

OTHER PUBLICATIONS

Chan, T.A., Morin, P.J., Vogelstein, B., and Kinzler, K.W. (1998). Mechanisms underlying non-steroidal antiinflammatory drug mediated apoptosis. Proc. Natl. Acad. Sci. U.S.A. 95, 681-686.
Dubois, R.N., Abramson, S.B., Crofford, L, Gupta, R.A., Simon, LS., Van De Putte, L.B., et al. (1998). Cyclooxygenase in biology, and disease. FASEB J. 12, 1063-1073.
Fueger, B. J., Czernin, J., Hildebrandt, I., Tran, C., Halpern, B.S., Stout, D., et al. (2006). Impact of animal handling on the results of 18F-FDG PET studies in mice. J. Nucl. Med. 47, 999-1006.
Fujita, T., Matsui, M., Takaku, K., Uetake, H., Ichikawa, W., Taketo, M.M., et al. (1998). Size-, and invasion- dependent increase in cyclooxygenase 2 levels in human colorectal carcinomas. Cancer Res. 58, 4823-4826.
Glynn, S. A., Prueitt, R. L., Ridnour, L.A., Boersma, B. J., Dorsey, T. M., Wink, D. A., et al. (2010). COX-2 activation is associated with Akt phosphorylation and poor survival in ER-negative, HER2-positive breast cancer. BMC Cancer 10:626. doi: 10.1186/1471-2407-10-626.
Harizi, H., Juzan, M., Pitard, V., Moreau, J.F., and Gualde,N. (2002). Cyclooxygenase-2-issued prostaglandin e(2) enhances the production of endogenous IL-10, which down-regulates dendritic cell functions. J. Immunol. 168, 2255-2263.
Harmey, J. H., Bucana, C. D., Lu, W., Byrne, A. M., McDonnell, S., Lynch, C., et al. (2002). Lipopolysaccharide-induced metastatic growth is associated with increased angiogenesis, vascular permeability and tumor cell invasion. Int. J. Cancer 101, 415-422.
Hida, T., Yatabe, Y., Achiwa, H., Muramatsu, H., Kozaki, K., Nakamura, S., et al. (1998). Increased expression of cyclooxygenase 2 occurs frequently in human lung cancers, specifically in adenocarcinomas. Cancer Res. 58, 3761-3764.
Hill, R., Li,Y., Tran, L. M., Dry, S., Calvopina, J. H., Garcia, A., et al. (2012). Cell intrinsic role of Cox-2 in pancreatic cancer development. Mol. Cancer Ther. doi: 10.1158/1535-7163.
Jalilian, A. R., Tabatabai, S. A., Shafiee, A., Afarideh, H., Najafi, R., and Bineshmarvasti, M. (2000). One-step, no-carrier-added synthesis of a 18F-labeled benzodiazepine recep—for ligand. J. Labelled Comp. Radiopharm. 43, 545555.
Kobukai, S., Kremers, G. J., Cobb, J. G., Baheza, R., Xie, J., Kuley, A., et al. (2011). Induction of antitumor immunity by dendritic cells loaded with MPA11P-conjugated mucin-1 peptide antigen. Transl. Oncol. 4, 1-8.
Loening, A. M., and Gambhir, S. S. (2003). AMIDE: a free soft-ware tool for multimodality medi-cal image analysis. Mol. Imaging 2, 131-137.
McCarthy, T. J., Sheriff, A. U., Graneto, M. J., Talley, J. J., and Welch, M. J. (2002). Radiosynthesis, in vitro validation, and in vivo evaluation of 18F-labeled COX-1 and COX-2 inhibitors. J. Nucl. Med. 43, 117-124.
Moore, B. C., and Simmons, D. L. (2000). COX-2 Inhibition, apoptosis and chemoprevention by non-steroidal anti-inflammatory inflammatory drugs. Curr. Med. Chem. 7, 1131-1144.
Mueller, K., Faeh, C., and Diederich, F. (2007). Fluorine in pharmaceuticals: looking beyond intuition. Science 317, 1881-1886.
Murata, H., Kawano, S., Tsuji, S., Tsuji, M., Sawaoka, H., Kimura, Y., et al. (1999). Cyclooxygenase-2 over-expression enhances lymphatic invasion and metastasis in human gastric carcinoma. Am. J. Gastroenterol. 94, 451-455.

(Continued)

*Primary Examiner* — Michael G Hartley
*Assistant Examiner* — Jagadishwar Samala
(74) *Attorney, Agent, or Firm* — Thomas Horstemeyer, LLP

(57) ABSTRACT

Embodiments of the present disclosure provide for a compound, methods of making a compound, a probe, methods of making a probe, pharmaceutical compositions including a probe or a compound, methods of using a probe, methods of imaging, diagnosing, localizing, monitoring, and/or assessing a disease (e.g., cancer, diseases caused by inflammation (e.g., arthritis, cardiovascular disease, and the like)), and the like, and/or related biological events using a probe, kit for imaging, diagnosing, localizing, monitoring, and/or assessing a disease, and/or related biological events, using a probe, and the like.

13 Claims, 4 Drawing Sheets

(56) References Cited

OTHER PUBLICATIONS

Muthuswamy, R., Mueller-Berghaus, J., Haberkorn, U., Reinhart, T. A., Schadendorf, D., and Kalinski, P. (2010). PGE (2) transiently enhances DC expression of CCR7 but inhibits the ability of DCs to produce CCL19 and attract naive T cells. Blood 116, 1454-1459.

Nagler, C., Hardt, C., Zanker, K. S., and Dittmar, T. (2011). Co-cultivation of murine BMDCs with 67NR mouse mammary carcinoma cells give rise to highly drug resistant cells. Cancer Cell Int. 11, 21.

Nasir, A., Lopez, A., Boulware, D., Malafa, M., and Coppola, D. (2011). Correlation between COX-2, and APC expression in left versus right-sided human colon cancer. Anticancer Res. 31, 2191-2195.

Nolting, D.D., Nickels, M., Price, R., Gore, J.C., and Pham, W. (2009). Synthesis of bicyclo[5.3.0]azulene derivatives. Nat.Protoc. 4, 1113-1117.

Pham, W., Weissleder, R., and Tung, C. H. (2002). An azulene dimer as a near-infrared quencher. Angew. Chem. Int. Ed. Engl. 41, 3659-3662, 3519.

Prabhakaran, J., Majo, V.J., Simpson, n. R., van Heertum, R.L., Mann, J.J., and Kumar, J. S. (2005). Synthesis of [11C]celecoxib: a potential PET probe for imaging COX-2 expression. J. Labelled Comp. Radiopharm. 48, 887-895.

Rouzer, C.A., and Marnett, L.J. (2009). Cyclooxygenases: structural, and functional insights. J. Lipid Res. 50(Suppl.), S29-S34.

Shimada, K, Anai, S., Marco, D.A., Fujimoto, K., and Konishi, N. (2011). Cyclooxygenase 2-dependent and independent activation of Akt through casein kinase 2alpha contributes to human bladder cancer cell survival. BMC Urol. 11:8. doi: 10.1186/1471-2490-11-8.

Singh, B., Cook, K. R., Vincent, L., Hall, C. S., Martin, C., and Lucci, A. (2011). Role of COX-2 in tumorospheres derived from a breast cancer cell line. J. Surg. Res. 168, e39-e49.

Sobolewski, C., Cerella, C., Dicato, M., Ghibelli, L., and Diederich, M. (2010). The role of cyclooxygenase-2 in cell proliferation and cell death in human malignancies. Int. J. Cell Biol. 215158.

Stolina, M., Sharma, S., Lin, Y., Dohadwala, M., Gardner, B., Luo, J., et al. (2000). Specific inhibition of cyclooxygenase 2 restores anti-tumor reactivity by altering the balance of IL-10 and IL-12 synthesis. J. Immunol. 164, 361-370.

Uddin, M. J., Crews, B. C., Blobaum, A. L., Kingsley, P. J., Gorden, D. L., McIntyre, J. O., et al. (2010). Selective visualization of cyclooxygenase-2 in inflammation and cancer by targeted fluorescent imaging agents. Cancer Res. 70, 3618-3627.

Uddin, M. J., Crews, B. C., Ghebre-selasie, K., Huda, L, Kingsley, P. J., Ansari, M. S., et al. (2011). Fluorinated cyclooxygnase-2 inhibitors as agents in PET imaging of inflammation and cancer. Cancer Prev. Res. 4, 1536-1545.

van Ryn, J., Trummlitz, G., and Pairet, M. (2000). COX-2 selectivity, and inflammatory processes. Curr. Med. Chem. 7, 1145-1161.

Xie, W. L., Chipman, J. G., Robertson, D. L., Erikson, R. L., and Simmons, D. L. (1991). Expression of a mitogen-responsive gene encoding prostaglandin synthase is regulated by mRNA splicing. Proc. Natl. Acad. Sci. U.S.A. 88, 2692-2696.

Yokota, K., Kusaka, M., Ohshima, T., Yamamoto, S., Kurihara, N., Yoshino, T., et al. (1986). Stimulation of prostaglandin E2 synthesis in cloned osteoblastic cells of mouse (MC3T3- E1) by epidermal growth factor. J. Biol. Chem. 26115410-15415.

* cited by examiner

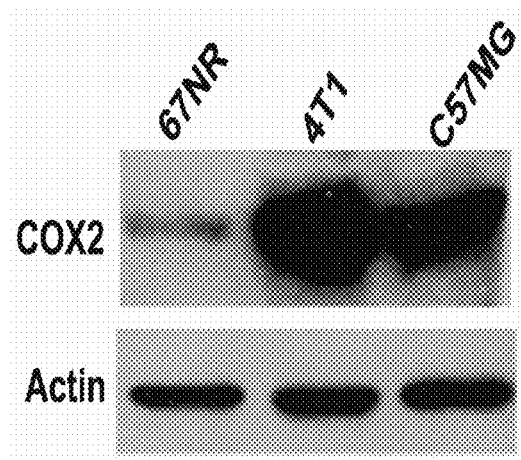
FIG. 3A
FIG. 3B
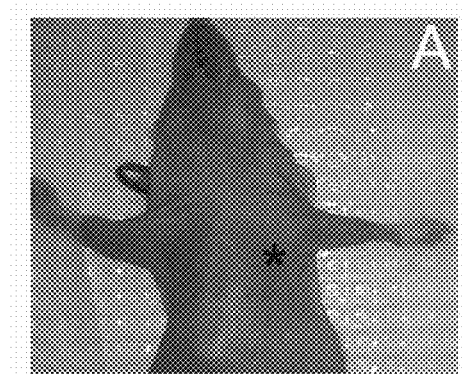
FIG. 4A
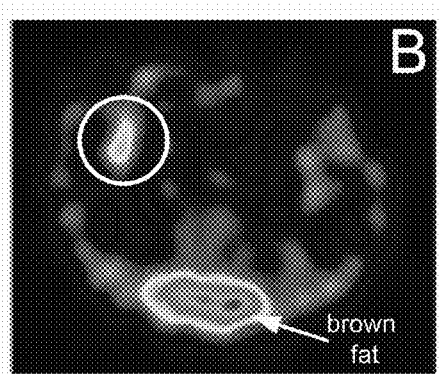
FIG. 4B
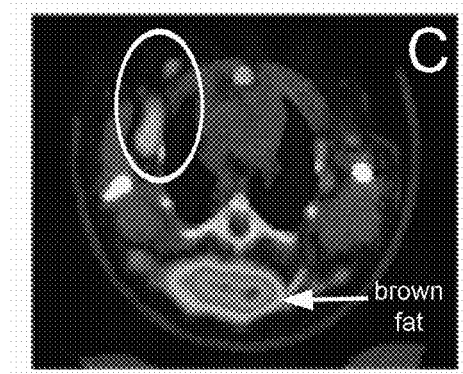
FIG. 4C
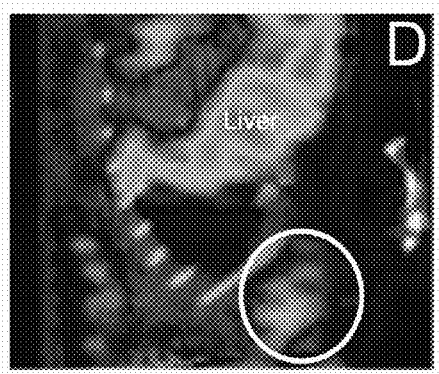
FIG. 4D

COMPOUNDS, PROBES, AND METHODS OF SYNTHESIS AND METHODS OF IMAGING COX-2-ASSOCIATED DISEASES

CROSS-REFERENCE TO RELATED APPLICATION

This application claims priority to U.S. provisional application entitled "COMPOUNDS, PROBES, AND METHODS OF SYNTHESIS AND METHODS OF IMAGING COX-2 DISEASES," having Ser. No. 61/724,495, filed on Nov. 9, 2012, which is entirely incorporated herein by reference.

FEDERAL SPONSORSHIP

This invention was made with Government support under Contract/Grant No. K01AG026366, awarded by the National Institute of Aging and Contract/Grant No. P50CA128323, awarded by the National Cancer Institute. The Government has certain rights in this invention.

BACKGROUND

Prostaglandin endoperoxide synthase, known more commonly as cyclooxygenase (COX), is the key enzyme required for the conversion of arachidonic acid to the biological mediators known as prostanoids, which include prostaglandins, prostacyclin, and thromboxane (Moore and Simmons, 2000). The two COX iso-forms, COX1 and COX2, are expressed in different tissue at varying degrees (Dubois et al., 1998). While COX1 is expressed under basal conditions in almost all tissues and is particularly important to the maintenance of gastric mucosal integrity, renal function, and hemostasis, COX2 is undetectable in most normal tissues (van Ryn et al., 2000). COX2 is highly inducible in cells involved in inflammation and cancer (Rouzer and Marnett, 2009). In addition to the role it plays in inflammation, several lines of research suggest that COX2 is involved in the early stage of tumorigenesis (Yokota et al., 1986; Xie et al., 1991). Notably, COX2 not only continues to express during tumor progress, but the expression of COX2 also indicates an aggressive tumor phenotype that behaves more invasively (Fujita et al., 1998) and thus, a poor prognosis (Sobolewski et al., 2010). COX2 overexpression has been well documented in several human carcinomas including colon (Nasir et al., 2011), stomach (Murata et al., 1999), lung (Hida et al., 1998), breast (Glynn et al., 2010; Singh et al., 2011), head and neck (Chan et al., 1998), bladder (Shimada et al., 2011), and pancreas (Hill et al., 2012). The relationship between cancers and increased COX2 activity provides a rationale for the use of COX2 as a prognostic marker and as a quantifiable indicator of tumor progression and treatment efficacy. Collectively, this approach could be achieved through in vivo imaging of COX2 activity, especially when using a sensitive imaging technique such as positron emission tomography (PET). A number of research initiatives have reported the development of COX2 probes with which to visualize cancer-related inflammation including its use in optical (Uddin et al., 2010) and PET imaging (McCarthy et al., 2002; Prabhakaran et al., 2005; Uddin et al., 2011). However, there is still a need to develop other probes to image COX2.

SUMMARY

Embodiments of the present disclosure provide for a compound, methods of making a compound, a probe, methods of making a probe, pharmaceutical compositions including a probe or a compound, methods of using a probe, methods of imaging, diagnosing, localizing, monitoring, and/or assessing a disease (e.g., cancer, diseases caused by inflammation (e.g., arthritis, cardiovascular disease, and the like)), and the like, and/or related biological events using a probe, kit for imaging, diagnosing, localizing, monitoring, and/or assessing a disease, and/or related biological events, using a probe, and the like.

An embodiment of the composition, among others, includes: a compound having the following structure:

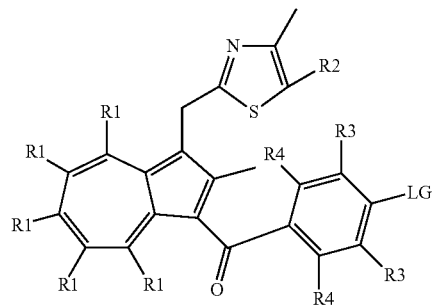

wherein LG is a leaving group selected from the group consisting of: $NO_2$, Br, I, Cl, F, and a quaternary amine group; wherein each R1 is independently selected from the group consisting of: H, halogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein R2 is selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein each R3 is independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl; and wherein each of R4 is independently selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl.

An embodiment of the composition, among others, includes: a probe having the following structure:

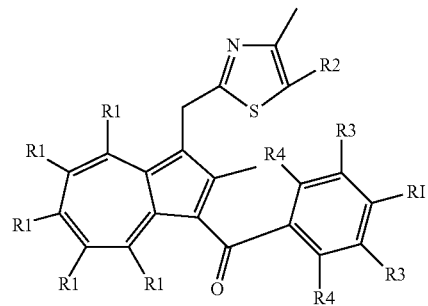

wherein RI is a radioisotope; wherein each R1 is independently selected from the group consisting of: H, halogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein R2 is selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein each R3 is independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl; and wherein each of R4 is independently selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl.

An embodiment of the method of diagnosing the presence of a disease in a subject, among others, includes: administering to the subject, a probe having the following structure:

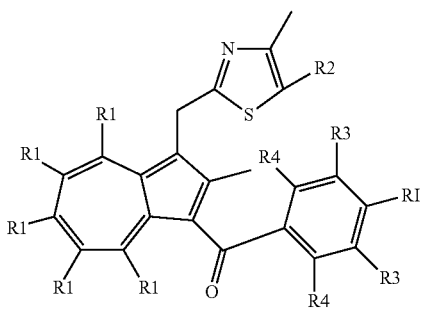

wherein RI is a radioisotope; wherein each R1 is independently selected from the group consisting of: H, halogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein R2 is selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein each R3 is independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl; and wherein each of R4 is individually selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl; imaging at least a portion of the tissue, cells, or the subject; and detecting the probe, wherein the location of the probe corresponds to a disease or related biological event.

An embodiment of the method of monitoring the progress of one or more melanin related diseases in a subject, among others, includes: contacting or administering to the subject a probe having the following structure:

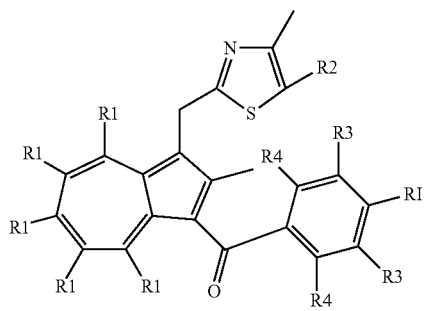

wherein RI is a radioisotope; wherein each R1 is independently selected from the group consisting of: H, halogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein R2 is selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein each R3 is independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl; and wherein each of R4 is individually selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl; imaging at least a portion of the tissue, cells, or the subject; and detecting the probe, wherein the location of the probe corresponds to a melanin related disease or related biological event, wherein the size of the location is monitored over time.

An embodiment of the method, among others, includes: forming the following structure:

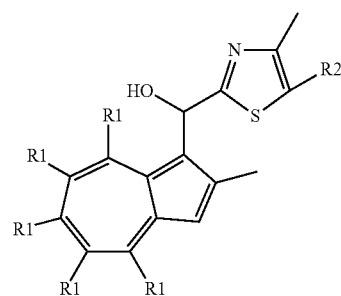

by reacting

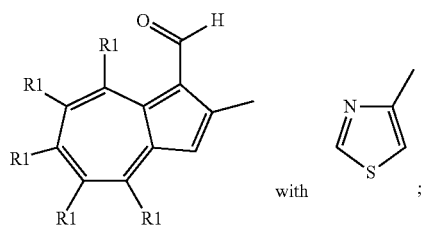

forming the following structure:

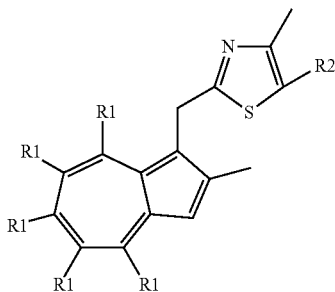

by performing a hydrogenolysis reaction on product of the proceeding step;
forming the following structure:

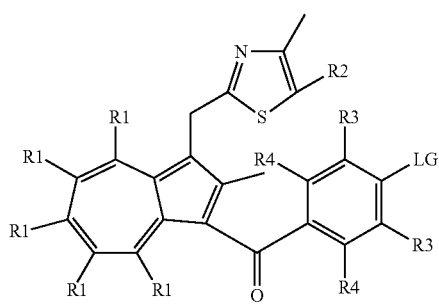

by performing a Friedel-Crafts acylation to attach an aromatic ring to position 3 of the azulene ring of the product of the proceeding step, wherein the aromatic ring has the following structure

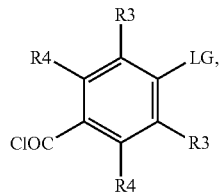

wherein LG is a leaving group selected from the group consisting of: $NO_2$, Br, I, Cl, quaternary amine group; wherein each R1 is independently selected from the group consisting of: H, halogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein R2 is selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein each R3 is independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl; and wherein each of R4 is individually selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl.

An embodiment of the method, among others, includes: forming the following structure:

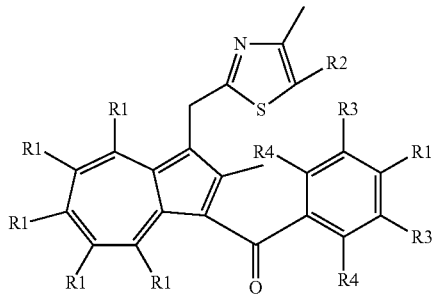

by reacting

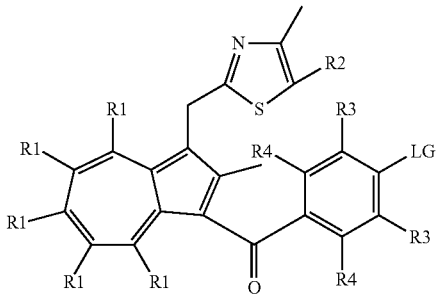

with $^{18}F/F^-$, 4,7,13,16,21,24-hexaoxa-1,10-diazabicyclo [8.8.8]-hexacosane, and dipotassium phosphate trihydrate; wherein LG is a leaving group selected from the group consisting of: $NO_2$, Br, I, Cl, quaternary amine group; RI is $^{18}F$; wherein each R1 is independently selected from the group consisting of: H, halogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein R2 is selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein each R3 is independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl; and wherein each of R4 is individually selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the FIG. 1 illustrates a schematic of the design of a convergent synthesis approach to develop an azulene-based $^{18}$F-COX2 probe 13 and its related precursors.

FIGS. 3A-3B illustrate the analysis of COX2 expression and quanity in murine breast cancer cells. Western blot analysis (FIG. 3A) was performed to verify the presence and relative intensity of COX2 in C57GM cells compared to other cells. β-actin served as a loading control. RT-PCR data (FIG. 3B) were used to quantify the level of COX2 expression after normalization.

FIGS. 4A-4D illustrate in vivo microPET imaging of COX2 in a tumor-bearing mouse model. At the time of imaging, tumor size was approximately 4 mm in diameter (*, tumor) (A). Representative PET image of an axial section showing tumor uptake of $^{18}$F-COX2 probe (white circle) (B). Fused PET/CT axial image (C). Fused PET/CT sagittal view of the tumor (D).

DETAILED DESCRIPTION

Figure 1:
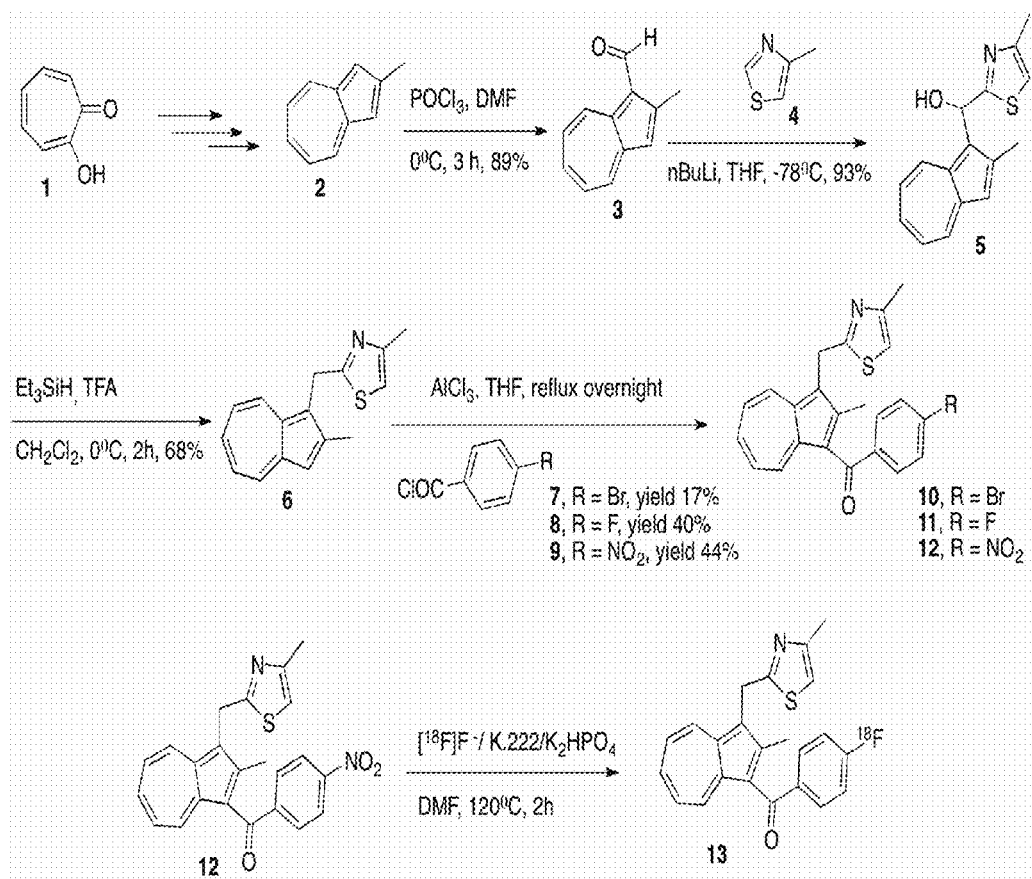

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, molecular imaging, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

The term "substituted" refers to any one or more hydrogens on the designated atom that can be replaced with a selection from the indicated group, provided that the designated atom's normal valence is not exceeded, and that the substitution results in a stable compound.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon which can be straight or branched, having 1 to 20 carbon atoms, wherein the stated range of carbon atoms includes each intervening integer individually, as well as sub-ranges. Examples of alkyl include, but are not limited to, methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon which can be straight or branched, containing at least one carbon-carbon double bond, having 2 to 20 carbon atoms, wherein the stated range of carbon atoms includes each intervening integer individually, as well as subranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "substituted," as in "substituted alkyl", and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below. The word "lower" refers to one to 4 carbons in the corresponding molecule.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

By "administration" is meant introducing a probe (also referred to as the "imaging agent") of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the probe of the present disclosure is defined as an amount sufficient to yield an acceptable image using equipment that is available for clinical use. A detectably effective amount of the probe of the present disclosure may be administered in more than one injection. The detectably effective amount of the probe of the present disclosure can vary according to factors such as the degree of susceptibility of the individual, the age, sex, and weight of the individual, idiosyncratic responses of the individual, and the like. Detectably effective amounts of the probe of the present disclosure can also vary according to instrument and film-related factors. Optimization of such factors is well within the level of skill in the art.

As used herein, the term "host" or "subject" includes humans, mammals (e.g., cats, dogs, horses, etc.). Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living host" refers to host or organisms noted above that are alive and are not dead. The term "living host" refers to the entire host or organism and not just a part excised (e.g., a liver or other organ) from the living host.

The term "sample" can refer to a tissue sample, cell sample, a fluid sample, and the like. The sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over the background signal.

The term "detectable signal" is a signal derived from noninvasive imaging techniques such as, but not limited to, positron emission tomography (PET) or single photon emission computed tomography (SPECT). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background.

"Cancer", as used herein, shall be given its ordinary meaning, as a general term for diseases in which abnormal cells divide without control. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

General Discussion

Embodiments of the present disclosure provide for a compound, methods of making a compound, a probe, methods of making a probe, pharmaceutical compositions including a probe or a compound, methods of using a probe, methods of imaging, diagnosing, localizing, monitoring, and/or assessing a disease (e.g., cancer, diseases caused by inflammation (e.g., arthritis, cardiovascular disease, and the like)), and the like, and/or related biological events using a probe, kit for imaging, diagnosing, localizing, monitoring, and/or assessing a disease, and/or related biological events, using a probe, and the like. In particular, the present disclosure includes methods relating to non-invasive imaging (e.g., positron emission tomography (PET) imaging) using a probe in vivo.

Embodiments of the present disclosure include methods for imaging tissue, cells, or a subject, that includes contacting with or administering to a tissue, cells, or subject, a probe, and imaging with a PET imaging system. The imaging can be performed in vivo and/or in vitro. In particular, embodiments of the present disclosure can be used to image a disease, such as cancer, diseases caused by inflammation, or related biological events. In this regard, the tissue, cells, or subject, can be tested to determine if the tissue, cells, or subject includes a disease and/or related biological events, monitor the progression (or regression) of the disease, or assess the response of the disease to treatment, image, and the like. In an embodiment, the tissue or cells can be within a subject or have been removed from a subject.

In an embodiment, the disease and/or related biological events can be imaged using probes of the present disclosure. In an embodiment, the disease and/or related biological event can include cancer, precancerous tissue or cells, and tumors. In an embodiment, the disease and/or related biological event can include diseases caused by inflammation processes such as: rheumatoid arthritis, whereby the presence and location of inflammation can be imaged; and cardiovascular diseases including atherosclerosis, ischemia, stroke, or thromboses, whereby plaques, areas at risk for acute occlusion as well as areas of hypoxia can be imaged.

In an embodiment, the probe can be imaged using imaging systems such as positron emission tomography (PET) imaging systems, single photon emission computed tomography (SPECT), and the like. In an embodiment, PET imaging is a preferred embodiment.

In an embodiment, the probe can have the following structure:

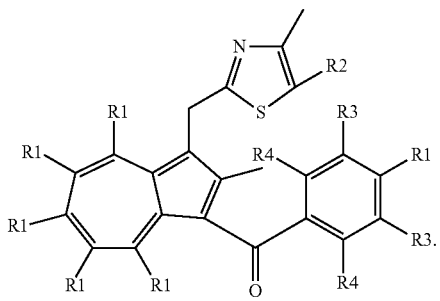

RI is a radioisotope. In an embodiment, the radioisotope is selected from the group consisting of: $^{18}F$, $^{131}I$, $^{125}I$, $^{124}I$, $^{123}I$, $^{77}Br$, $^{77}Br$, $^{75}Br$, and $^{75}Br$. In a specific embodiment, the probe includes a radioisotope, $^{18}F$, that can be used to detect, image, or otherwise identify the probe, quantify the amount of the probe, determine the location of the probe (e.g., in imaging), and combinations thereof. Fluorine-18 ($t_{1/2}$=109.7 min; $\beta^+$, 99%) is an ideal short-lived PET isotope for labeling small molecules.

In an embodiment, each R1 can be independently selected from the group consisting of: hydrogen, a halogen, a substituted or unsubstituted alkyl group, a substituted or unsubstituted alkenyl, a substituted or unsubstituted alkyny, a substituted or unsubstituted aryl, and a substituted or unsubstituted heteroaryl. In an embodiment, R2 can be selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl. In a particular embodiment, each of R1 and each of R2 can be independently selected from: hydrogen, a halogen, a substituted or unsubstituted $C_1$ to $C_4$ hydrocarbon.

In an embodiment, each R3 (ortho position to LG) can be independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl. In particular, each R3 can be independently selected from: hydrogen, an aldehyde, and a substituted or unsubstituted $C_1$ to $C_4$ hydrocarbon.

In an embodiment, each R4 (meta position to LG) can be independently selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl. In particular, each R4 can be independently selected from: hydrogen, an aldehyde, a methoxy, a substituted or unsubstituted $C_1$ to $C_4$ hydrocarbon.

In an embodiment, R1, R2, R3, and/or R4 can each be the same or different. In an embodiment, each of R1, R2, R3, and R4 can be independently selected from hydrogen, halogen, or a substituted or unsubstituted $C_1$ to $C_4$ hydrocarbon.

In particular, the probe can have the following structure:

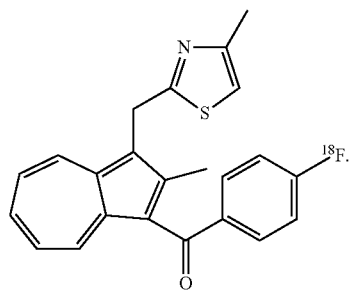

In an embodiment, the probe can be present in a composition or a pharmaceutical composition, in an amount to achieve the desired results (e.g., image a disease or related biological event).

In an embodiment, the probe can be formed by reacting the compound represented by the following structure:

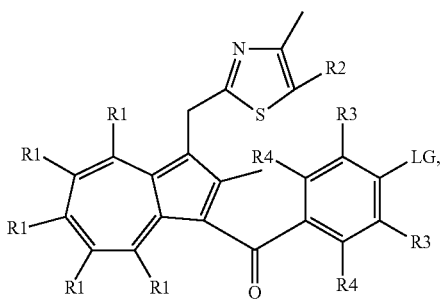

with $^{18}F/F^-$, 4,7,13,16,21,24-hexaoxa-1,10-diazabicyclo [8.8.8]-hexacosane, and dipotassium phosphate trihydrate. Additional details are provided in the Example. Although the Example describes a specific compound, the synthesis can be applicable to the more general structure that includes R1, R2, R3, R4, and LG. Also, in another embodiment, another radioisotope can replace LG. In addition, solvents and other reactants noted in the Example can be replaced by other appropriate solvents and reactants to produce the desired probe. In addition, conditions like temperature, pH, and reaction time can be adjusted as desired to produce the desired probe. In an embodiment, the probe can be present in a composition or a pharmaceutical composition, in an amount to achieve the desired results.

An embodiment of the present disclosure includes a compound with the following structure:

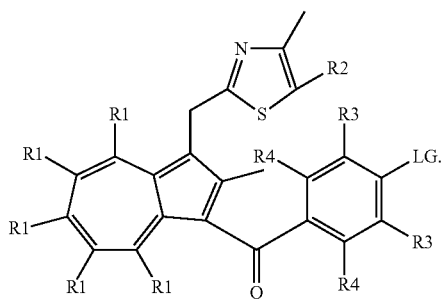

In an embodiment, each of R1, R2, R3, and R4 are the same as the R1, R2, R3, and R4 described above in reference to the probe. In an embodiment, R1, R2, R3, and/or R4 can each be the same or different. In an embodiment, LG is a leaving group and can be selected from the group consisting of: $NO_2$, Br, I, Cl, quaternary amine groups (e.g., trimethyl ammonium triflate salt), and the like. In an embodiment, each of R1, R2, R3, and R4 can be independently selected from hydrogen, halogen, or a substituted or unsubstituted $C_1$ to $C_4$ hydrocarbon, while LG can be selected from the group consisting of: $NO_2$, Br, I, Cl, and quaternary amine groups. In particular, the compound can have the following structure:

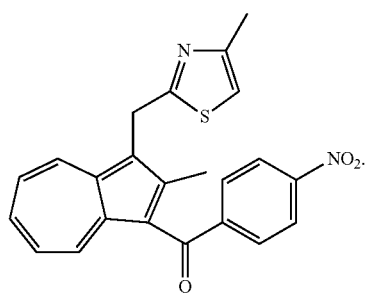 [SMILES: Cc1csc(Cc2c3cccccc-3c(C(=O)c3ccc([N+](=O)[O-])cc3)c2C)n1]

In general, the compound,

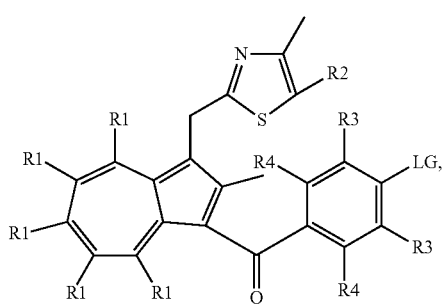

can be formed by the following synthesis. The synthesis is described very broadly and additional details for forming a specific embodiment of the compound are provided in the Example. Although the Example describes a specific compound, the synthesis can be applicable to the more general structure that includes R1, R2, R3, R4, and LG. In addition, solvents and other reactants noted in the Example can be replaced by other appropriate solvents and reactants to produce the desired intermediates and compound. In addition, conditions like temperature, pH, and reaction time can be adjusted as desired to produce the desired intermediates and compound.

In an embodiment, an intermediate having the following structure:

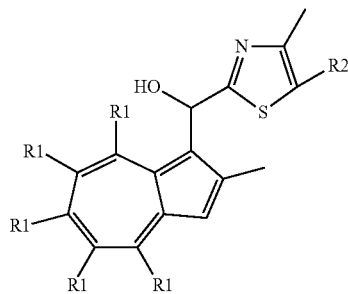

can be formed by reacting

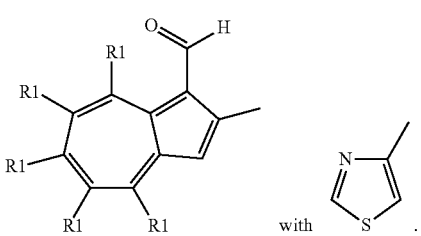

In an embodiment, 4-methyl thiazole can be mixed with THF (alternatively, methylene chloride chloroform, ethylacetate, and the like) and cooled to about −78° C. for about 20-30 minutes prior to mixing with nBuLi over the course of about 15 minutes and kept at about −78° C. Next the mixture was mixed with 2-methylazulene-1-carbaldehyde for about 15-30 minutes at about −78° C. and then warmed to room temperature. The extracts can be further processed as described in the Example.

In an embodiment, an intermediate having the following structure:

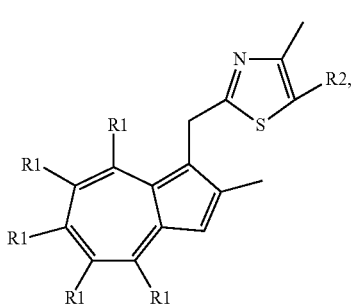

can be formed by performing a hydrogenolysis reaction (e.g., using triethylsilane and trifluoroacetic acid) on the product of the proceeding step for about 2 hours at about 0° C. The mixture can be further processed as described in the Example.

In an embodiment, an intermediate having the following structure:

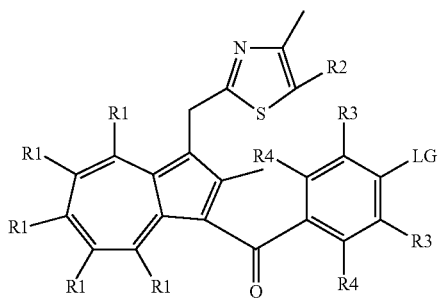

can be formed by performing a Friedel-Crafts acylation to attach an aromatic ring to position 3 of the azulene ring of the product of the proceeding step, where the aromatic ring has the following structure

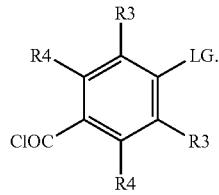

The mixture can be further processed as described in the Example. As described above, the compound can be synthesized to form the probe as described above.

Methods of Use

Embodiments of this disclosure include, but are not limited to: methods of imaging tissue, cells, or a subject using probe of the present disclosure; methods of imaging a disease and/or related biological events, using a probe of the present disclosure; methods of diagnosing a disease or related biological events using a probe of the present disclosure; methods of monitoring the progress of a disease or related biological events using a probe of the present disclosure; and the like.

Embodiments of the present disclosure can be used to image, detect, study, monitor, evaluate, assess, and/or screen, the disease and/or related biological events, in particular, cancer, diseases caused by inflammation, in vivo or in vitro using a probe of the present disclosure.

In general, the probe can be used in imaging cancer and/or diseases caused by inflammation. For example, the probe is provided or administered to a subject in an amount effective to result in uptake of the probe into the disease or tissue of interest. The subject is then introduced to an appropriate imaging system (e.g., PET system) for a certain amount of time. The cells or tissue that takes up the probe could be detected using the imaging system. The location of the detected signal from the probe can be correlated with the location of the disease(s).

The steps of this method can be repeated at determined intervals so that the location and/or size of the disease can be monitored as a function of time and/or treatment. In particular, the probe can find use in a host undergoing chemotherapy, for example, or other treatment (e.g., using a drug), to aid in visualizing the response of a disease or tumor to the treatment. In this embodiment, the probe is typically visualized and sized prior to treatment, and periodically during chemotherapy to monitor the tumor size.

Embodiments of the probe also find use as a screening tool in vitro to select compounds for use in treating diseased tissue or cells. The disease could be easily monitored by incubating the cells with the disease with the probe during or after incubation with one or more candidate drugs. The ability of the drug compound to affect the disease can be imaged over time using the probe.

It should be noted that the amount effective to result in uptake of the probe into the cells or tissue of interest will depend upon a variety of factors, including for example, the age, body weight, general health, sex, and diet of the host; disease type and stage; the time of administration; the route of administration; the rate of excretion of the specific probe employed; the duration of the treatment; the existence of other drugs used in combination or coincidental with the specific composition employed; and like factors well known in the medical arts.

Kits

The present disclosure also provides packaged compositions or pharmaceutical compositions comprising a pharmaceutically acceptable carrier and a probe of the present disclosure. In certain embodiments, the packaged compositions or pharmaceutical composition includes the reaction precursors to be used to generate the compound or the probe according to the present disclosure. Other packaged compositions or pharmaceutical compositions provided by the present disclosure further include indicia including at least one of: instructions for using the probe to image a host, or host samples (e.g., cells or tissues), which can be used as an indicator of conditions including, but not limited to, melanin related disease and biological related events.

Embodiments of this disclosure encompass kits that include, but are not limited to, the compound or the probe and directions (written instructions for their use). The components listed above can be tailored to the particular biological event to be monitored as described herein. The kit can further include appropriate buffers and reagents known in the art for administering various combinations of the components listed above to the host cell or host organism. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like.

Dosage Forms

Embodiments of the present disclosure can be included in one or more of the dosage forms mentioned herein. Unit dosage forms of the pharmaceutical compositions (the "composition" includes at least a probe or compound of the present disclosure) of this disclosure may be suitable for oral, mucosal (e.g., nasal, sublingual, vaginal, buccal, or rectal), parenteral (e.g., intramuscular, subcutaneous, intravenous, intra-arterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

Typical compositions and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Embodiments of the present disclosure include pharmaceutical compositions that include a probe, pharmaceutically acceptable salts thereof, with other chemical components, such as physiologically acceptable carriers and excipients. One purpose of a pharmaceutical composition is to facilitate administration of a probe to an organism.

Embodiments of the present disclosure may salts and these salts are within the scope of the present disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when an embodiment of the present disclosure contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an active compound may be formed, for example, by reacting an active compound with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

The amounts and specific type of active ingredient (e.g., probe or compound) in a dosage form may differ depending on various factors. It will be understood, however, that the total daily usage of the compositions of the present disclosure will be decided by the attending physician or other attending professional within the scope of sound medical judgment. The specific effective dose level for any particular host will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Brief Introduction

The overall objectives of this research are to (i) develop azulene-based positron emission tomography (PET) probes and (ii) image COX2 as a potential biomarker of breast cancer. Several lines of research have demonstrated that COX2 is over expressed in breast cancer and that its presence correlates with poor prognoses. While other studies have reported that COX2 inhibition can be modulated and used beneficially as a chemopreventive strategy in cancer, no viable mechanism for achieving that approach has yet been developed. This shortfall could be circumvented through in vivo imaging of COX2 activity, particularly using sensitive imaging techniques such as PET. Toward that goal, our laboratory focuses on the development of novel 18F-labeled COX2 probes. We began the synthesis of the probes by transforming tropolone into alactone, which was subjected to an [8+2]cycloaddition reaction to yield 2-methylazulene as the core ring of the probe. After exploring numerous synthetic routes, the final target molecule and precursor PET compounds were prepared successfully using convergent synthesis. Conventional 18F labeling methods caused pre-cursor decomposition, which prompted us to hypothesize that the acidic protons of the methylene moiety between the azulene and thiazole rings were readily abstracted by a strong base such as potassium carbonate. Ultimately, this caused the precursors to disintegrate. This observation was supported after successfully using an 18F labeling strategy that employed a much milder phosphate buffer. The 18F-labeled COX2 probe was tested in a breast cancer xenograft mouse model. The data obtained via successive whole body PET/CT scans indicated probe accumulation and retention in the tumor. Overall, the probe was stable invivo and node fluorination was observed. A biodistribution study and Western blo tanalysis corroborate with the imaging data. In conclusion, this novel COX2 PET probe was shown to be a promising agent for cancer imaging and deserves further investigation.

Introduction:

Prostaglandin endoperoxide synthase, known more commonly as cyclooxygenase (COX), is the key enzyme required for the conversion of arachidonic acid to the biological mediators known as prostanoids, which include prostaglandins, prostacyclin, and thromboxane (Moore and Simmons, 2000). The two COX iso-forms, COX1 and COX2, are expressed in different tissue at varying degrees (Dubois et al., 1998). While COX1 is expressed under basal conditions in almost all tissues and is particularly important to the maintenance of gastric mucosal integrity, renal function, and hemostasis, COX2 is undetectable in most normal tissues (van Ryn et al., 2000). COX2 is highly inducible in cells involved in inflammation and cancer (Rouzer and Marnett, 2009). In addition to the role it plays in inflammation, several lines of research suggest that COX2 is involved in the early stage of tumorigenesis (Yokota et al., 1986; Xie et al., 1991). Notably, COX2 not only continues to express during tumor progress, but the expression of COX2 also indicates an aggressive tumor phenotype that behaves more invasively (Fujita et al., 1998) and thus, a poor prognosis (Sobolewski et al., 2010). COX2 overexpression has been well documented in several human carcinomas including colon (Nasir et al., 2011), stomach (Murata et al., 1999), lung (Hida et al., 1998), breast (Glynn et al., 2010; Singh et al., 2011), head and neck (Chan et al., 1998), bladder (Shimada et al., 2011), and pancreas (Hill et al., 2012). The relationship between cancers and increased COX2 activity provides a rationale for the use of COX2 as a prognostic marker and as a quantifiable indicator of tumor progression and treatment efficacy. Collectively, this approach could be achieved through in vivo imaging of COX2 activity, especially when using a sensitive imaging technique such as positron emission tomography (PET). A number of research initiatives have reported the development of COX2 probes with which to visualize cancer-related inflammation including its use in optical (Uddin et al., 2010) and PET imaging (McCarthy et al., 2002; Prabhakaran et al., 2005; Uddin et al., 2011). Our laboratory has focused on the development of azulene-based COX2 probes owing to the nanomolar affinity and high selectivity toward the COX2 enzyme reported previously (Tomiyama et al., 1999). Azulene has a structural backbone similar to indomethacin and sulindac, two of the most common non-steroidal anti-inflammatory drugs (NSAIDs). However, the difference between such NSAIDs and this non-benzenoid aromatic hydrocarbon is the existence of a 7-member ring. According to Tomiyama et al. (1999) azulene is suitable for COX2 development since the larger ring fits well within the larger binding pocket of COX2 compared to COX1, which enhances COX2 selectivity.

Herein, we describe a novel chemistry approach that uses a con-vergent synthesis methodology to develop azulene-based COX2 PET probes. Of note, we synthesized the main azulene ring using the procedure we reported previously (Pham et al., 2002; Nolting et al., 2009). The two other ring structures were assembled onto the azulene ring using commercially available analogs. To retain the biological activity as reported by Tomiyama et al. (1999), we designed the precursors specifically with 18 F fluoride labeling in mind Not only do we prefer this isotope due to its relatively long half-life, but also because replacing a hydrogen atom with a fluorine is likely to not affect biological activity since they are very similar sterically (Jalilian et al., 2000; Mueller et al., 2007). We also report herein, to our knowledge, the first time, a modified labeling condition that uses dipotassium phosphate ($K_2HPO_4$) for this family of compounds, which we found to be unstable using the conventional PET labeling process. Overall, the chemical yield of this 7-step synthesis of the nitro precursor 12 (FIG. 1) is 25%. The biodistribution results and small animal PET imaging demonstrate the potential use of the 18 F-COX2 probe in breast cancer imaging.

Materials and Methods

Chemicals and Characterization

We synthesized 2-methyl azulene 2 and reported that outcome in previous publications (Pham et al., 2002; Nolting et al., 2009). All reagents were obtained through commercial sources such as Sigma-Aldrich, Acros, or Tokyo Chemical Industry (TCI) and were used without further purification. Solvents were purified using the PureSolv MD purification system. All reactions were conducted in argon-flushed, rubber septum-sealed flasks, and the reagents were introduced via tight-gas syringes. Reaction progress was monitored by thin layer chromatography (TLC) on pre-coated silica gel plates. Visualization was accomplished by the naked eyes and by 254 nm-UV light. Flash chromatography separations were performed using Biotage and Teledyne systems. HPLC analysis and purification were performed using diode array Hitachi LaChrome Elite® systems. 1H NMR and 13 C NMR spectra were recorded on a Bruker 400 MHz spectrometer in $CDCl_3$ using tetramethylsilane (TMS) as the internal standard. All chemical shifts were reported in ppm.

2-Methylazulene-1-carbaldehyde (Compound 3)

$POCl_3$ (3.86 mL, 42.2 mmol) was added slowly to a stirring dimethylformamide (DMF) solution at 0° C. The mixture was cooled for 1 h before a DMF solution of 2-methyl azulene (2.0 g, 14.1 mmol) was added drop-wise. The reaction was mixed for 2 h at 0° C., and then quenched with cold 10% NaOH. The organic layer was extracted into ethyl acetate after which the extracts were washed with water and brine, dried with $MgSO_4$ and purified using flash chromatography (ethyl acetate and hexane). The purified material was dried down into a dark red solid. Yield: 2.389 g, 89%. $^1H$ NMR (400 MHz, $CDCl_3$) δ 10.50 (s, $^1H$), 9.44 (d, J=9.73 Hz, $^1H$), 8.29 (d, J=9.72 Hz, $^1H$), 7.72 (t, J=9.82 Hz, 1H), 7.56 (t, J=9.82 Hz, $^1H$), 7.46 (t, J=9.67 Hz, $^1H$), 7.08 (s, $^1H$), 2.84 (s, $^3H$); $^{13}C$ NMR (100 MHz, $CDCl_3$) δ 185.8, 154.9, 144.4, 142.1, 137.9, 136.4, 129.7, 128.5, 122.5, 120.3, 15.1. HRMS (ES) calcd. MH+ ($C_{12}H_{11}O$) 171.0732 found 171.0804.

(2-Methylazulen-1-yl)(4-methylthiazol-2-yl)methanol (compound 5)

4-Methyl thiazole 4 (837 µL, 9.2 mmol) was added to 20 mL of tetrahydrofuran (THF). The mixture was cooled to −78° C. and stirred for 20 min. Afterward, 2.5 M nBuLi (2.45 mL, 6.1 mmol) was added slowly over the course of 15 min. The resultant mixture was stirred at −78° C. for 1 h, after which a freshly made solution of 2-methylazulene-1-carbaldehyde 3 (522 mg, 3.1 mmol) in THF was added slowly at −78° C. The reaction was stirred for 30 min and checked by TLC (50:50 Hexanes/EtOAc). Hexane was added at −78° C. and the reaction was warmed to room temperature. Water was added to quench the reaction and the organic layer was extracted into ethyl acetate. The extracts were washed with water and brine, dried with $MgSO_4$ and purified using flash chromatography (ethyl acetate and hexane). The purified material was dried down into a purple solid. Yield: 768 mg, 93%. $^1H$ NMR (400 MHz, $CDCl_3$) δ 8.45 (d, J=9.85 Hz, $^1H$), 8.19 (d, J=9.54 Hz, $^1H$), 7.52 (t, J=9.82 Hz, $^1H$), 7.19-7.13 (m, $^3H$), 6.78 (s, $^1H$), 6.64 (s, $^1H$), 2.56 (s, $^3H$), 2.42 (s, $^3H$); $^{13}C$ NMR (100 MHz, $CDCl_3$) δ 174.2, 152.2, 149.1, 140.6, 137.2, 136.1, 134.8, 132.4, 125.3, 123.8, 123.6, 118.7, 114.1, 67.8, 16.9, 15.6. HRMS (ES) 152.2, 149.1, 140.6, 137.2, 136.1, 134.8, 132.4, 125.3, 123.8, 123.6, 118.7, 114.1, 67.8, 16.9, 15.6. HRMS (ES) calcd. $[M-H_2O^+H]^+$ ($C_{16}H_{14}NS$) 252.0925. found 252.0836.

4-Methyl-2-((2-methylazulen-1-yl)methyl)thiazole (compound 6)

Triethylsilane (178 µL, 1.11 mmol) was added slowly to 2 mL of trifluoroacetic acid (TFA) at room temperature. The mixture was cooled to 0° C. and mixed for 30 min. A fresh solution of (2-methylazulen-1-yl)(4-methylthiazol-2-yl) methanol 5 (100 mg, 0.371 mmol) in dichloromethane was then added slowly to the mixture being stirred at 0° C. The reaction was kept at 0° C. for 2 h and then warmed to room temperature. Afterward, the mixture was poured into cold 20% KOH to quench the reaction. The organic layer was extracted into diethyl ether and washed with water and brine, dried with $MgSO_4$ and purified using flash chromatography (ethyl acetate and hexane). The purified material was dried down into a blue solid. Yield: 64.3 mg, 68%. $^1H$ NMR (400 MHz, $CDCl_3$) δ 8.19 (t, J=10.38 Hz, 2H), 7.49 (t, J=9.90 Hz, 1H), 7.21 (s, $^1H$), 7.17-7.10 (m, 2H), 6.60 (s, 1H), 4.68 (s, 2H), 2.60 (s, 3H), 2.42 (s, 3H); $^{13}C$ NMR (100 MHz, $CDCl_3$) δ 171.8, 152.1, 149.0, 140.1, 137.0, 135.8, 134.4, 131.5, 123.2, 122.7, 117.8, 113.1, 29.3, 17.0, 15.0. HRMS (ES) calcd. MH+ $[C_{16}H_{16}NS]^+$ 254.0925. found 254.0990.

(2-Methyl-3-((4-methylthiazol-2-yl)methyl)azulen-1-yl)

(4 nitrophenyl)methanone (compound 12)

$AlCl_3$ (101 mg, 0.757 mmol) was weighed quickly into an argon-flushed vial. While the vial was being purged with argon, dichloroethane was added slowly. The ensuing mixture was syringed quickly into a round-bottom flask and cooled to 0° C. A solution of 4-nitro benzoyl chloride (70 mg, 0.377 mmol) in dichloroethane was added slowly into the suspension of $AlCl_3$ at O—C. This mixture was stirred at 0° C. for 30 min after which a fresh solution of compound 6 (64 mg, 0.253 mmol) in dichloroethane was added slowly to the reaction mixture being stirred at 0° C. After the reaction was stirred at 0° C. for 30 min, it was brought to room temperature and then stirred for another 30 min. The reaction was quenched by adding ice-cold water slowly. The organic layer was extracted into dichloromethane and washed with water and brine, dried with $MgSO_4$ and purified using flash chromatography (ethyl acetate and hexane). The purified material was dried down into a brown/orange solid. Yield: 45 mg, 44%. $^1H$ NMR (400 MHz, $CDCl_3$) δ 8.63 (d, J=9.84 Hz, $^1H$), 8.44 (d, J=9.89 Hz, $^1H$), 8.29 (d, J=8.82 Hz, $^2H$), 7.86 (d, J=8.81 Hz, $^2H$), 7.71 (t, J=9.82 Hz, $^1H$), 7.46 (t, J=9.72 Hz, $^1H$), 7.29 (t, J=9.93 Hz, $^1H$), 6.67 (s, 1H), 4.70 (s, $^2H$), 2.42 (s, $^3H$), 2.39 (s, $^3H$); $^{13}C$ NMR (100 MHz, $CDCl^3$) δ 192.2, 170.3, 152.3, 150.4, 149.5, 146.3, 141.4, 140.2, 138.2, 135.6, 133.7, 130.2, 127.2, 125.0, 124.3, 123.6, 123.3, 113.2, 29.0, 16.9. HRMS (ES) calcd MH+ $[C_{23}H_{19}N_2O_3S]$+403.1038. found 403.1106.

Labeling Synthesis

No-carrier-added [18 F]F− (3.46 Ci) from a cyclotron was isolated from [$^{18}O]H_2O$ by trapping it in a small MP1 fluoride trap and release cartridge that has been conditioned with water and air-dried. The [$^{18}F]F^-$ was then eluted with an acetonitrile/water mixture containing 20 mg of Kryptofix 222 and 5.0 mg of dipotassium phosphate trihydrate ($K_2HPO_4.3H_2O$) into a conically shaped reaction vial previously purged with helium. The [$^{18}F]F^-$ solution was evaporated under a small stream of helium at 100° C. after which the residue was dried by azeotropic evaporation with anhydrous acetonitrile to ensure anhydrous reaction conditions were maintained for $^{18}F$ labeling. After precursors 10 or 12 (2-3 mg, each) were added to the reaction vial, the resultant mixture was heated to 110° C. for 15 min. After cooling to 30° C. the reaction mixture was diluted with 4.4 mL of mobile phase (60% EtOH/$H_2O$) and loaded onto a C-18 semi-preparative column (Macherey-Nagel C-18 250×10 mm) The flow rate was increased from 0 to 6 mL/min over a 3 min time period. The 6 mL/min flow rate was maintained for 35 min during which the radioactive product was collected (28-31 min). The contents corresponding to the radioactive peak were diluted with 100 mL of distilled water and loaded onto a C-18 Sep-Pak® pre-conditioned with ethanol and water. The Sep-Pak was eluted by hand with 1 mL of 200 proof ethanol followed by 9 mL of saline. Qualitative control of the radioactive product was performed using radio-HPLC (C-18 column, Varian Dynamax, 4.6×250 mm, 30-75% gradient water to acetonitrile over 35 min, flow rate 1 mL/min) to confirm [$^{18}$F]fluoride incorporation. The retention time was compared to that of the "cold" standard compound 11 (retention time=20.4 min).

Cell Culture and Tumor Implantation

Murine breast cancer cells, C57MG, 4T1, and 67NR were used as reported previously (Kobukai et al., 2011). Briefly, the cells were cultured and maintained in Dulbecco modified Eagle medium (Mediatech, Manassas, Va., USA) in the presence of 10% fetal calf serum (FCS; Invitrogen, Carlsbad, Calif., USA), penicillin-streptomycin antibiotics (Mediatech), and 10 mg/mL insulin (Sigma-Aldrich, St Louis, Mo., USA) at 37° C. and 5% $CO_2$ incubator.

The experimental protocol for animal imaging was approved by the Vanderbilt Medical Center Institutional Animal Care and Use Committee. Nude mice 6-8 weeks of age (n=8, from Jackson Laboratory, Bar Harbor, Me., USA) were implanted subcutaneously under anesthesia (isoflurane mixed with 2% oxygen) with 1.0×106 C57MG cells in the mammary fat pad. The progress of tumor growth was monitored via every-other-day measurement of tumor size and animal weight. When the tumors reached approximately 4 mm in diameter, in vivo PET imaging was performed.

IC50 Assay

Various concentrations of the $^{19}$F-COX2 compound ranging from 0.1 μM to 0.3 nM were dispensed into designated wells within a 96-well microtiter plate at a final volume of 220 μL per well. Each well contained an assay buffer, heme, and ovine COX2 provided in Cayman's colorimetric COX inhibitor screening assay kit. In addition to the tested probe, the assay condition was accompanied by background control wells and the 100% initial activity wells. Five minutes after incubation of all assay components at 25° C., an arachidonic acid substrate at a final concentration of 100 μM and the colorimetric co-substrate N,N,N',N'-tetramethyl-p-phenylenediamine were added to each well. The plate was then incubated at 25° C. for an additional 5 min before reading the absorbance at 590 nm using a plate reader. Absorbance of the duplicate assay of each well was averaged and subtracted from the 100% initial activity sample, after which it was divided by the 100% initial activity sample and multiplied by 100 to arrive at the percentage of inhibition.

Positron Emission Tomography

Positron emission tomography imaging was performed using the microPET Focus 220 (Siemens Pre-clinical, Knoxville, Tenn., USA) in a static acquisition mode for 30 min at 60, 120, and 150 min after injection of $^{18}$F-COX2 probe 13 (150-200 μCi, 100-130 μL) into awake, non-fasted mice (n=8) via the tail vein. To obtain whole-body scans, mice were placed in a supine position. The data were acquired in a 3-D mode with an axial span of approximately 8 cm. During the scanning, the animals were anesthetized using isoflurane and the temperature inside the scanner was maintained at 30° C. using a pad connected to a circulating warm water bath. After PET imaging, a CT image was acquired using the microCAT II (Siemens Pre-clinical, Knoxville, Tenn., USA) using the same animal holder with the subjects maintained under anesthesia throughout, and then the mice were immediately euthanized upon completion of the CT scan. PET images were reconstructed using the iterative MAP reconstruction algorithm with 18 iterations and a beta smoothing value of 0.001 into 128×128×95 slices with a voxel size of 0.475 mm×0.475 mm×0.796 mm. The PET and CT images were co-registered using the imaging tool AMIDE (Loening and Gambhir, 2003).

Biodistribution

After the imaging session, the mice were euthanized and hearts, muscles, blood, livers, spleens, kidneys, stomachs, brains, intestines, tumors, and lungs were retrieved. The tissues were weighed and assessed for 18 F radioactivity using a gamma counter (CRC-15W, Capintec, Ramsey, N.J., USA).

Western Blot

Cells were washed twice with PBS, and lysed in ice-cold lysis buffer (50 mM Tris-HCl, pH7.4, 0.5% Triton X-100, 0.25% NP-40, 0.25% Na deoxycholate, 0.1% SDS, 150 mM NaCl, 1 mM EDTA), supplemented with complete anti-protease cocktail (Sigma). After removing nuclear and insoluble debris at 16,000 g for 20 min, the supernatant designated as whole cell lysate (WCL) was saved. Protein concentrations were determined with Bradford method (Bio-Rad assay, Bio-Rad, Hercules, Calif., USA). Thirty micrograms of WCL proteins were separated by 12% sodium dodecyl sulfate polyacrylamide gel electrophoresis (SDS-PAGE) and transferred onto polyvinylidene difluoride membranes (PVDF, Biorad). Membranes were blocked with 5% dry milk in Tris-buffered Saline with 0.1% Tween-20 (TBST) and immunoblotted overnight at 4° C. with primary antibodies against COX2. β-Tubulin antibody (Santa Cruz) was used to blot same membrane for loading control. After washing with TBST three times, horse radish peroxidase (HRP) conjugated secondary antibodies were added for 1 h incubation. After wash with TBST twice and once with TBS, the protein bands were detected with an enhanced chemiluminescence (Pierce, Rockford, Ill., USA) by exposure to films (Kodak) for 30 s. Band intensity was quantified by using NIH Image J software.

Real-Time PCR

Total RNA was isolated and purified from cultured cells by using the Qiagen RNAeasy kit. RNA (2 mg) was reversibly transcribed by Superscript II (Invitrogen) with oligo-(dT) as primer to generate single stranded cDNA by following manufacturer recommended protocols. Quantitation of mRNA (cDNA) levels for COX2 was carried out by real-time PCR using 516P as internal controls. Real-time PCR primers were designed by web-based OligoPerfect™ Designer (Invitrogen). The primer pairs used in PCR are forward 51-CAG-GAGAGAAGGAAATGGC-31 (SEQ ID NO: 1) and backward 51-TGAGGAGAACAGATGGGATT-3' (SEQ ID NO: 2) to yield a 184 nt product. Real-time PCR was carried out with the SYBR-green mixture from Bio-Rad in a final volume of 25 μL, with initial denaturation at 94° C. for 3 min, followed by 45 cycles of denaturation at 94° C. for 10 s, annealing and extension at 65° C. for 1 min. PCR products were verified by acrylamide gel electrophoresis, melting curve analysis.

Results

Chemical Synthesis and Confirmation of the 18 F-COX2 Probe

Starting with tropolone 1, we synthesized three analogs of the precursor as shown in FIG. 1. The advantage of working with azulene is that the reaction progress can be monitored via color changes. For example, evidence that compound 2 was converted to an aldehyde 3 using the Vilsmeier-Haack reaction resulted in a color change from blue to red. The thiazole ring was incorporated onto azulene in two steps. This included a hydrogenolysis reaction using triethylsilane in the presence of TFA to yield compound 6, which is blue. Finally, we used Friedel-Crafts acylation to attach an aromatic ring to position 3 of the azulene. This reaction was completed using dichloroethane at room temperature for 30 min, which yielded the final product, which is brown. Under reaction conditions similar to those used with p-nitrobenzoyl chloride, 4-bromobenzoyl chloride provided an average yield of only 17% for the resultant Friedel-Crafts acylation product. The seemingly low yield can be attributed to the weak electron-withdrawing group. From an electronic perspective, we noted that the fluoro moiety is a much more favorable alternative than its bromo counterpart, as the fluoro derivative possesses greater electronegativity and is thus suitable for generating reactive electrophilic acylium ions. Notably, it is important to perform the Friedel-Crafts reaction as the last step since the nitro precursors will be reduced to amino groups under the reduction conditions. Compounds 10 and 12 were designed for [$^{18}$F]fluoride labeling while compound 11 was used as a control to confirm the radiolabeling product and for specific activity analysis. All of the intermediates and products were characterized fully by $^1$H NMR and $^{13}$C NMR and mass spectrometry.

$^{18}$F-COX2 Probe

We found this family of azulene compounds to be unstable under conventional $^{18}$F labeling conditions. After exhaustively analyzing every single reagent, solvent, and temperature involved in the labeling experiment, which included Kryptofix, Dimethyl sulfoxide (DMSO), DMF, acetonitrile, and potassium carbonate, we found by HPLC analysis that potassium carbonate was decomposing precursors 10 and 12 instantaneously at room temperature. This undesired chemical transformation was easily visualized since the color changed from brown to black when the precursors came into contact with potassium carbonate. Although we did not analyze the intermediates, this undesired reaction could be attributed to the acidic methylene protons between the azulene and thiazole ring, which may be sensitive to potassium carbonate. To overcome this problem, we decided to use a milder buffer such as dipotassium phosphate, which works perfectly for this purpose.

Although there was no sign of decomposition after we optimized the labeling conditions, the labeling of the bromo precursor 10 was sluggish. In contrast, we labeled successfully the nitro derivative 12, albeit with low yield (3%, decay corrected) at EOS with >99% chemical and radiochemical purities and with a specific activity of 733 Ci/mmol.

The Specificity of the $^{19}$F-COX2 Compound for the COX2 Enzyme

Figure 2:
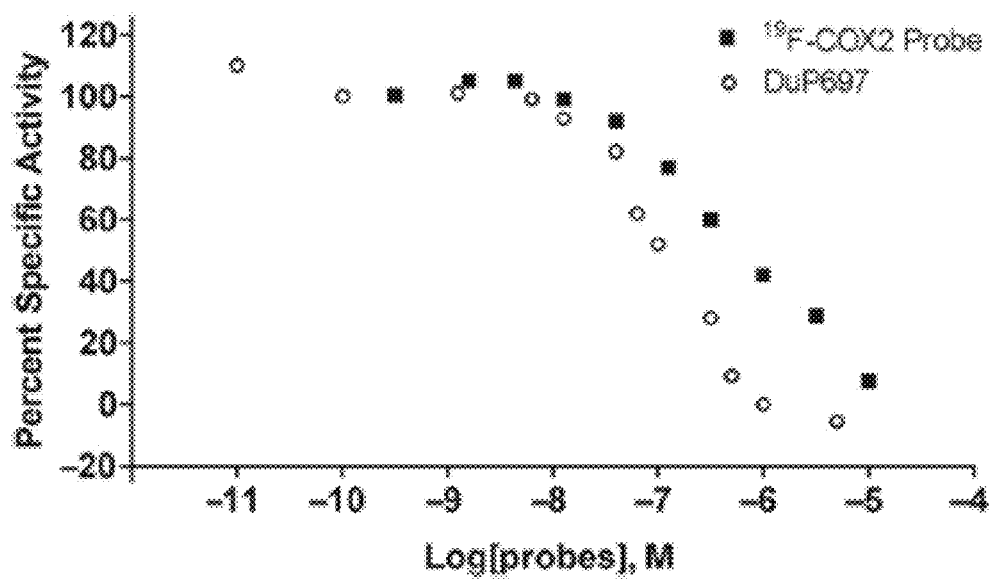
FIG. 2 shows a graph that illustrates the specificity of the $^{19}$F-COX2 probe for the COX2 enzyme.

In addition to being synthesized for use in facilitating the confirmation of the $^{18}$F-labeled product, the cold compound 11 was also used to assess the IC50 value. The assay was performed using 10 duplicate concentrations in a range comparable to DuP697, a known COX2 inhibitor. As shown in FIG. 2, the Hill slopes of the curves that represent $^{19}$F-COX2 and DuP697 are −0.62 and −1.0, respectively; suggesting the specificity of the synthesized PET probe for COX2. After taking the background signal into account, the IC50 value of the $^{19}$F-COX2 compound was 661 nM.

COX2 is Overexpressed in C57Mg Breast Cancer Cells

To confirm and quantify COX2 expression in the C57MG cell line, we selected two other cells, 4T1 and 67NR, which are also murine breast cancer cell lines. It has been demonstrated previously that the 4T1 (Harmey et al., 2002) and 67NR cells (Nagler et al., 2011) were positive and negative, respectively, for COX2. As shown in FIG. 3A, Western blot analysis on cell lysate indicated a very low level of COX2 in 67NR cells. In contrast, C57MG possesses a high constitutive level of COX2. Furthermore, real-time PCR data demonstrated that COX2 was expressed at a rate approximately 31-fold higher in C57MG cells compared to 67NR (FIG. 3B).

In Vivo Imaging of COX2 in Tumor Mouse Model and Biodistribution

Figure 5:
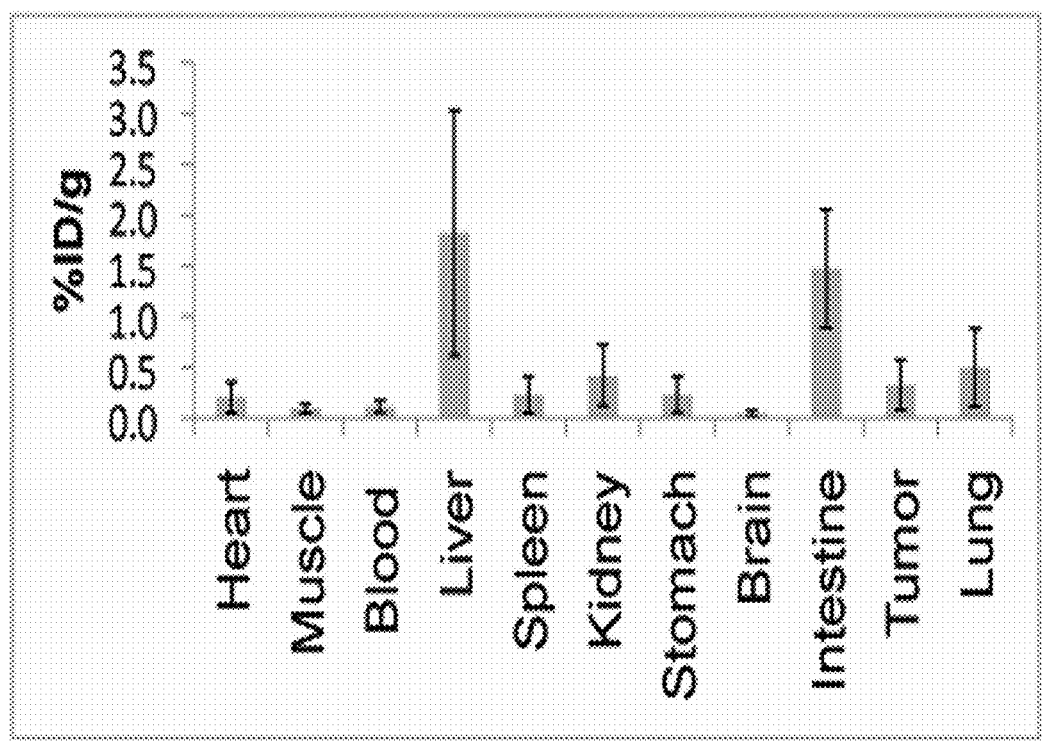
FIG. 5 illustrates a graph of the uptake (% injection dose/g tissue) of the $^{18}$F-COX2 probe 13 in a non-fasted tumor-bearing mice (n=3).

To assess the specificity of the probes for the detection of COX2 expression, we performed in vivo PET imaging of non-fasted mice in which C57MG tumors had been implanted on the mammary fat pads. We monitored the distribution of the probe in breast cancer at several times after the intravenous bolus injection. The optimal emission data were collected during a static, whole-body scan 150 min after administration of the probe. PET and PET/CT images showed accumulation and retention of the $^{18}$F-COX2 probe 13 and that significant accumulation in the tumor resulted in high signal intensity compared to the background (p<0.05; FIGS. 4A-4D). The PET data corroborates with Western blot and RT-PCR analysis. We also observed a predominant hepatic uptake of the probe. That outcome is reasonably understandable since lipophilic compounds tend to possess a strong affinity for the liver. In addition, the high liver-bowel activity observed in this study suggests the possibility of hepatobiliary excretion. The probe exhibited negligible signal in the bone, thus eliminating the notion of in vivo defluorination. FIG. 5 shows the probe's biodistribution in non-fasted tumor-bearing mice (n=3) at 150 min post injection. The data shows that the probe accumulated in the tumor; however, the highest uptake was detected in the liver, followed by the intestine. It is very likely that the high activity observed in the intestine can be attributed partially to the stool residuals.

Discussion

The goal of this work is to design, synthesize and test a novel class of azulene-based probes with which to image COX2 in cancer. Although synthesis of this class of COX2 inhibitors has been reported in the past (Tomiyama et al., 1999), conversion from an inhibitor to a contrast agent requires an entirely different chemistry. This is because the chemistry used originally is unsuitable for producing the nitro precursor 12. Conversion of a nitrile derivative into thioamide using hydrogen sulfide, shown by Tomiyama et al. (1999), concomitantly reduces the nitro to an amine. Another disadvantage of constructing the thioamide directly from the azulene ring is that the process requires many steps of synthesis, and failure in any single step in the link will affect the whole scheme. In this project, we utilized a convergent synthesis strategy wherein the three major rings of the compound were either synthesized or acquired from a diverse library of analogs commercially. These were then assembled into the desired product using simple chemistry. Thanks to this approach, we shortened the synthesis by three or four steps. In addition, the approach enables the potential generation of a library of compounds with novel functional groups that offer untapped bioisosteres.

Another innovative approach of this work lies in the $^{18}$F labeling process. To our knowledge, currently, there are no reported data showing an alternative buffer to the conventional use of potassium carbonate. We hypothesized that the role played by potassium is that of serving as a counter-ion for the [$^{18}$F]fluoride and as such it can be displaced by a similar cation. However, for these precursors or any basic sensitive compounds, weaker bases such as dipotassium phosphate should be used as an alternative since their pH is nearly neutral. Since we have not performed this sort of experiment on other types of compounds, we cannot extrapolate the reason why the specific activity of final product is low. More work is under progress to improve the specific activity of compound 13. One approach in that direction is to use high-grade dipotassium phosphate to ensure the elimination of trace fluoride in the labeling process. Nevertheless, in view of our recent findings and in light of the high number of basic sensitive precursors that failed in PET labeling, it is appropriate to hope that this finding can provide far-reaching applications for other compounds.

In vivo PET imaging demonstrated that there was no defluorination of the probe in vivo even 2.5 h post injection of the radioligand. To our knowledge, this is the first COX2 PET radioligand demonstrating such high stability in vivo. However, as the scope of this article was to report the chemical development of the probe, future studies will be needed to fully characterize this radioligand in vivo which include blood sampling and kinetic modeling as well as displacement studies. In addition, other important issues still need further evaluation. For example, we do not have information regarding tumor uptake between fasted and non-fasted mice. Although there is no systematic or mechanism that explains the difference between these two groups of study, Fueger et al. (2006) reported that in fasted mice, tumor uptake increased fourfold while tumor-to-organ ratios increased up to 17-fold compared to the non-fasted counterparts. Currently, work is in progress in our group to address this issue. Further-more, in vivo blocking studies using cold compound 11 or COX2 inhibitors would be ideal to further confirm the specificity of this PET probe.

Data obtained in this work suggest that this probe not only has the potential to detect inflammation, but it can also be used to detect the early onset of cancer. Furthermore, this targeted imaging approach is applicable for the assessment of tumor response during chemotherapy. Another application for the in vivo imaging of COX2 lies in cell therapy. Muthuswamy et al. (2010) showed that COX2 impairs the ability of dendritic cells (DCs) to attract naïve T cells. One of the mechanisms involved is that COX2 inhibits the ability of DCs to produce CCL19. In another study, Harizi et al. (2002) showed that COX2 induced PGE2 enhances the production of endogenous IL-10, which downregulates DC functions. By using COX2 inhibitors to attenuate the expression of IL-10 and the concomitant restoration of IL-12 production by DCs, Stolina et al. (2000) demonstrated that the COX2 inhibitor can modulate and be used beneficially as an adjuvant strategy in cancer therapy. Altogether, we believe that non-invasive imaging of COX2 with this probe in breast cancer would provide valuable insight into the tumor microenvironment.

In conclusion, we have demonstrated an innovative synthetic approach to the development of a novel class of $^{18}$F-COX2 contrast agents. In addition, we reported on the optimized labeling conditions that can be applied to any base-sensitive PET precursors. The chemistry we utilized is reproducible and scalable, and each step of the syntheses described in this work has been repeated and characterized more than 30 times by NMR and mass spectrometry. Most importantly, small animal PET imaging data suggest the specificity of the probe for COX2. In general, it seems reasonably certain that this class of azulene-based agents deserves further evaluation, as in vivo imaging of COX2 will offer significant insights into the implication of this enzyme in the inflammation-dysplasia-cancer matrix.

REFERENCES, EACH OF WHICH IS INCORPORATED HEREIN BY REFERENCE

Chan, T. A., Morin, P. J., Vogelstein, B., and Kinzler, K. W. (1998). Mechanisms underlying non-steroidal antiinflammatory drug mediated apoptosis. Proc. Natl. Acad. Sci. U.S.A. 95, 681-686.

Dubois, R. N., Abramson, S. B., Crofford, L., Gupta, R. A., Simon, L S., Van De Putte, L. B., et al. (1998). Cyclooxygenase in biology, and disease. FASEB J. 12, 1063-1073.

Fueger, B. J., Czernin, J., Hildebrandt, I., Tran, C., Halpern, B. S., Stout, D., et al. (2006). Impact of animal handling on the results of 18F-FDG PET studies in mice. J. Nucl. Med. 47, 999-1006.

Fujita, T., Matsui, M., Takaku, K., Uetake, H., Ichikawa, W., Taketo, M. M., et al. (1998). Size-, and invasion-dependent increase in cyclooxygenase 2 levels in human colorectal carcinomas. Cancer Res. 58, 4823-4826.

Glynn, S. A., Prueitt, R. L., Ridnour, L. A., Boersma, B. J., Dorsey, T. M., Wink, D. A., et al. (2010). COX-2 activation is associated with Akt phosphorylation and poor survival in ER-negative, HER2-positive breast cancer. BMC Cancer 10:626. doi: 10.1186/1471-2407-10-626

Harizi, H., Juzan, M., Pitard, V., Moreau, J. F., and Gualde, N. (2002). Cyclooxygenase-2-issued prostaglandin e(2) enhances the production of endogenous IL-10, which down-regulates dendritic cell functions. J. Immunol. 168, 2255-2263.

Harmey, J. H., Bucana, C. D., Lu, W., Byrne, A. M., McDonnell, S., Lynch, C., et al. (2002). Lipopolysaccharide-induced metastatic growth is associated with increased angiogenesis, vascular permeability and tumor cell invasion. Int. J. Cancer 101, 415-422.

Hida, T., Yatabe, Y., Achiwa, H., Muramatsu, H., Kozaki, K., Nakamura, S., et al. (1998). Increased expression of cyclooxygenase 2 occurs frequently in human lung cancers, specifically in adenocarcinomas. Cancer Res. 58, 3761-3764.

Hill, R., Li, Y., Tran, L. M., Dry, S., Calvopina, J. H., Garcia, A., et al. (2012). Cell intrinsic role of Cox-2 in pancreatic cancer development. Mol. Cancer. Ther. doi: 10.1158/1535-7163 [Epub ahead of print].

Jalilian, A. R., Tabatabai, S. A., Shafiee, A., Afarideh, H., Najafi, R., and Bineshmarvasti, M. (2000). One-step, no-carrier-added synthesis of a 18F-labeled benzodiazepine receptor ligand. J. Labelled Comp. Radiopharm. 43, 545-555.

Kobukai, S., Kremers, G. J., Cobb, J. G., Baheza, R., Xie, J., Kuley, A., et al. (2011). Induction of antitumor immunity by dendritic cells loaded with MPA11P-conjugated mucin-1 peptide antigen. Transl. Oncol. 4, 1-8.

Loening, A. M., and Gambhir, S. S. (2003). AMIDE: a free soft-ware tool for multimodality medi-cal image analysis. Mol. Imaging. 2, 131-137.

McCarthy, T. J., Sheriff, A. U., Graneto, M. J., Talley, J. J., and Welch, M. J. (2002). Radiosynthesis, in vitro validation, and in vivo evaluation of 18F-labeled COX-1 and COX-2 inhibitors. J. Nucl. Med. 43, 117-124.

Moore, B. C., and Simmons, D. L. (2000). COX-2 Inhibition, apoptosis and chemoprevention by non-steroidal anti-inflammatory drugs. Curr. Med. Chem. 7, 1131-1144.

Mueller, K., Faeh, C., and Diederich, F. (2007). Fluorine in pharmaceuticals: looking beyond intuition. Science 317, 1881-1886.

Murata, H., Kawano, S., Tsuji, S., Tsuji, M., Sawaoka, H., Kimura, Y., et al. (1999). Cyclooxygenase-2 over-expression enhances lymphatic invasion and metastasis in human gastric carcinoma. Am. J. Gastroenterol. 94, 451-455.

Muthuswamy, R., Mueller-Berghaus, J., Haberkorn, U., Reinhart, T. A., Schadendorf, D., and Kalinski, P. (2010). PGE(2) transiently enhances DC expression of CCR7 but inhibits the ability of DCs to produce CCL19 and attract naive T cells. Blood 116, 1454-1459.

Nagler, C., Hardt, C., Zanker, K. S., and Dittmar, T. (2011). Co-cultivation of murine BMDCs with 67NR mouse mammary carcinoma cells give rise to highly drug resistant cells. Cancer Cell Int. 11, 21.

Nasir, A., Lopez, A., Boulware, D., Malafa, M., and Coppola, D. (2011). Correlation between COX-2, and APC expression in left versus right-sided human colon cancer. Anticancer Res. 31, 2191-2195.

Nolting, D. D., Nickels, M., Price, R., Gore, J. C., and Pham, W. (2009). Synthesis of bicyclo[5.3.0]azulene derivatives. Nat. Protoc. 4, 1113-1117.

Pham, W., Weissleder, R., and Tung, C. H. (2002). An azulene dimer as a near-infrared quencher. Angew. Chem. Int. Ed. Engl. 41, 3659-3662, 3519.

Prabhakaran, J., Majo, V. J., Simpson, N. R., van Heertum, R. L., Mann, J. J., and Kumar, J. S. (2005). Synthesis of [11C]celecoxib: a potential PET probe for imaging COX-2 expression. J. Labelled Comp. Radiopharm. 48, 887-895.

Rouzer, C. A., and Marnett, L. J. (2009). Cyclooxygenases: structural, and functional insights. J. Lipid Res. 50(Suppl.), S29-S34.

Shimada, K., Anai, S., Marco, D. A., Fujimoto, K., and Konishi, N. (2011). Cyclooxygenase 2-dependent and independent activation of Akt through casein kinase 2alpha contributes to human bladder cancer cell survival. BMC Urol. 11:8. doi: 10.1186/1471-2490-11-8

Singh, B., Cook, K. R., Vincent, L., Hall, C. S., Martin, C., and Lucci, A. (2011). Role of COX-2 in tumorospheres derived from a breast cancer cell line. J. Surg. Res. 168, e39-e49.

Sobolewski, C., Cerella, C., Dicato, M., Ghibelli, L., and Diederich, M. (2010). The role of cyclooxygenase-2 in cell proliferation and cell death in human malignancies. Int. J. Cell Biol. 215158.

Stolina, M., Sharma, S., Lin, Y., Dohadwala, M., Gardner, B., Luo, J., et al. (2000). Specific inhibition of cyclooxygenase 2 restores antitumor reactivity by altering the balance of IL-10 and IL-12 synthesis. J. Immunol. 164, 361-370.

Tomiyama, T., Tomiyama, I., and Yokota, M. (1999). Preparation of azulene derivatives as COX-2 inhibitors. JP 11302266:JP 1998-115303.

Uddin, M. J., Crews, B. C., Blobaum, A. L., Kingsley, P. J., Gorden, D. L., McIntyre, J. O., et al. (2010). Selective visualization of cyclooxygenase-2 in inflammation and cancer by targeted fluorescent imaging agents. Cancer Res. 70, 3618-3627.

Uddin, M. J., Crews, B. C., Ghebre-selasie, K., Huda, I., Kingsley, P. J., Ansari, M. S., et al. (2011). Fluorinated cyclooxygnase-2 inhibitors as agents in PET imaging of inflammation and cancer. Cancer Prev. Res. 4, 1536-1545.

van Ryn, J., Trummlitz, G., and Pairet, M. (2000). COX-2 selectivity, and inflammatory processes. Curr. Med. Chem. 7, 1145-1161.

Xie, W. L., Chipman, J. G., Robertson, D. L., Erikson, R. L., and Simmons, D. L. (1991). Expression of a mitogen-responsive gene encoding prostaglandin synthase is regulated by mRNA splicing. Proc. Natl. Acad. Sci. U.S.A. 88, 2692-2696.

Yokota, K., Kusaka, M., Ohshima, T., Yamamoto, S., Kurihara, N., Yoshino, T., et al. (1986). Stimulation of prostaglandin E2 synthesis in cloned osteoblastic cells of mouse (MC3T3-E1) by epidermal growth factor. J. Biol. Chem. 26115410-15415.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measurement technique and the type of numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim at least the following:

1. A composition, comprising: a compound having the following structure:

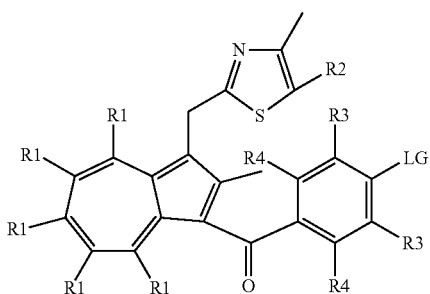

wherein LG is a leaving group selected from the group consisting of: $NO_2$, and a quaternary amine group; wherein each R1 is independently selected from the group consisting of: H, halogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein R2 is selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein each R3 is independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl; and wherein each of R4 is independently selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl.

2. The composition of claim 1, wherein each R1 is hydrogen.

3. The composition of claim 1, wherein each R3 is hydrogen.

4. The composition of claim 1, wherein each R4 is hydrogen.

5. The composition of claim 1, wherein each R1 is independently selected from the group consisting of: H, halogen, and a substituted or unsubstituted alkyl group; wherein R2 is selected from the group consisting of: hydrogen, and a substituted or unsubstituted alkyl group; wherein each R3 is independently selected from the group consisting of: hydrogen, an aldehyde, and a substituted or unsubstituted alkyl group; and wherein each R4 is independently selected from the group consisting of: hydrogen, an aldehyde, a methoxy, and a substituted or unsubstituted alkyl group.

6. The composition of claim 1, wherein the compound has the following structure:

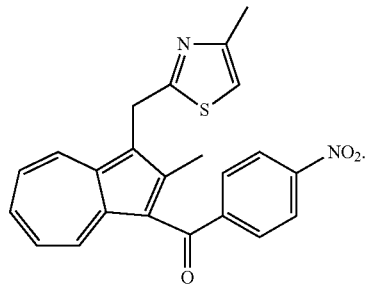 [SMILES: Cc1csc(Cc2c3cccccc-3c(C(=O)c3ccc([N+](=O)[O-])cc3)c2C)n1]

7. The composition of claim 1, wherein the composition is a pharmaceutical composition.

8. A composition, comprising: a probe having the following structure:

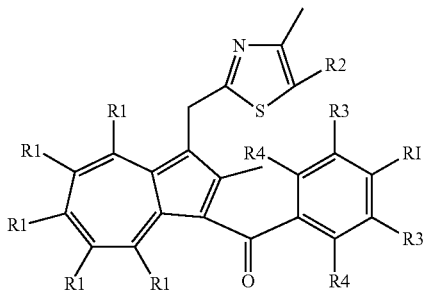

wherein RI is a radioisotope F, I, or Br; wherein each R1 is independently selected from the group consisting of: H, halogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein R2 is selected from the group consisting of: hydrogen, a substituted or unsubstituted alkyl group, a substituted or unsubstituted alkenyl, a substituted or unsubstituted alkyny, a substituted or unsubstituted aryl, and a substituted or unsubstituted heteroaryl; wherein each R3 is independently selected from the group consisting of: hydrogen, an aldehyde, a substituted or unsubstituted alkyl group, a substituted or unsubstituted alkenyl, a substituted or unsubstituted alkyny, a substituted or unsubstituted aryl, and a substituted or unsubstituted heteroaryl; and wherein each of R4 is independently selected from the group consisting of: hydrogen, an aldehyde, a methoxy, a substituted or unsubstituted alkyl group, a substituted or unsubstituted alkenyl, a substituted or unsubstituted alkyny, a substituted or unsubstituted aryl, and a substituted or unsubstituted heteroaryl.

9. The composition of claim 8, wherein the radioisotope is selected from the group consisting of: $^{18}F$, $^{131}I$, $^{125}I$, $^{124}I$, $^{123}I$, $^{121}I$, $^{77}Br$, $^{77}Br$, $^{75}Br$, and $^{75}Br$.

10. The composition of claim 8, wherein the radioisotope is $^{18}F$.

11. The composition of claim 8, wherein each R1 is independently selected from the group consisting of: H, halogen, and a substituted or unsubstituted alkyl group; wherein R2 is selected from the group consisting of: hydrogen, and a substituted or unsubstituted alkyl group; wherein each R3 is selected from the group consisting of: hydrogen, an aldehyde, and a substituted or unsubstituted alkyl group; and wherein each of R4 is independently selected from the group consisting of: hydrogen, an aldehyde, a methoxy, and a substituted or unsubstituted alkyl group.

12. The composition of claim 8, wherein the probe has the following structure:

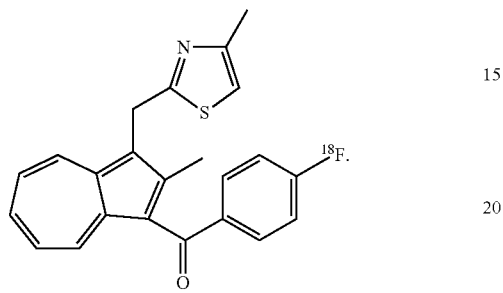

13. The composition of claim 8, wherein the composition is a pharmaceutical composition.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial sequence
<220> FEATURE:
<223> OTHER INFORMATION: Chemically synthesized forward primer

<400> SEQUENCE: 1
caggagagaa ggaaatggc                                              19

<210> SEQ ID NO 2
<211> LENGTH: 20
<212> TYPE: DNA
<213> ORGANISM: Artificial sequence
<220> FEATURE:
<223> OTHER INFORMATION: Chemically synthesized reverse primer
```

```
<400> SEQUENCE: 2
tgaggagaac agatgggatt                                            20
```